US008339596B2

(12) United States Patent
Sivertsen et al.

(10) Patent No.: US 8,339,596 B2
(45) Date of Patent: Dec. 25, 2012

(54) DEVICE AND METHOD FOR CONTACTLESS DETECTION OF CHARACTERISTICS OF CONTINUOUSLY DELIVERED TRANSLUCENT PRODUCTS

(75) Inventors: Agnar Holten Sivertsen, Tromsø (NO); Karsten Heia, Tromsø (NO); Heidi Anita Nilsen, Tromsdalen (NO)

(73) Assignee: Nordischer Maschinenbau Rud. Baader GmbH + Co.KG, Luebeck (DE)

( * ) Notice: Subject to any disclaimer, the term of this patent is extended or adjusted under 35 U.S.C. 154(b) by 45 days.

(21) Appl. No.: 12/919,825

(22) PCT Filed: Feb. 20, 2009

(86) PCT No.: PCT/EP2009/001359
§ 371 (c)(1),
(2), (4) Date: Aug. 27, 2010

(87) PCT Pub. No.: WO2009/112158
PCT Pub. Date: Sep. 17, 2009

(65) Prior Publication Data
US 2011/0013181 A1    Jan. 20, 2011

(30) Foreign Application Priority Data
Mar. 8, 2008   (DE) .......................... 10 2008 013 525

(51) Int. Cl.
*G01N 21/89* (2006.01)
(52) U.S. Cl. .................................................. 356/239.1
(58) Field of Classification Search .... 356/239.1–239.8, 356/238.1–238.3, 426–431; 250/225, 223 R, 250/391; 209/577, 587, 639, 938
See application file for complete search history.

(56) References Cited

U.S. PATENT DOCUMENTS

| | | | |
|---|---|---|---|
| 4,706,336 A | | 11/1987 | Hartmann et al. |
| 5,617,076 A | * | 4/1997 | Stern ............................. 340/583 |
| 6,207,946 B1 | * | 3/2001 | Jusoh et al. ................ 250/208.1 |

(Continued)

FOREIGN PATENT DOCUMENTS
WO    WO-2006/075164 A    7/2006

OTHER PUBLICATIONS
International Search Report From PCT/EP2009/001359 Dated May 28, 2009 With English Translation.

*Primary Examiner* — Sang Nguyen
(74) *Attorney, Agent, or Firm* — Venable LLP; Robert Kinberg; Ryan M. Flandro

(57) ABSTRACT

An apparatus for contactless detection of characteristics of continuously conveyed, translucent products includes first and second transmitting units each having an independent light source to generate high-intensity light radiation to illuminate the product, a light-converting element to form a planar light field from the light radiation and a focusing element to form a line of light running transversely to a direction of conveying of the products from the planar light field. A receiving unit has a detection device to pick up the light radiation transflected by the product. Shading elements are arranged respectively between the transmitting units and the receiving unit. The first transmitting unit is arranged in front of the receiving unit in the direction of conveying of the products and the second transmitting unit is arranged behind the receiving unit in the direction of conveying.

19 Claims, 3 Drawing Sheets

U.S. PATENT DOCUMENTS

| | | | |
|---|---|---|---|
| 6,252,189 B1 * | 6/2001 | Campbell | 209/581 |
| 6,624,883 B1 * | 9/2003 | Zhou et al. | 356/237.1 |
| 7,262,380 B1 * | 8/2007 | Ulrichsen et al. | 209/577 |
| 7,538,871 B2 * | 5/2009 | Frick et al. | 356/326 |
| 7,557,920 B2 * | 7/2009 | Lebens | 356/394 |
| 7,982,876 B2 * | 7/2011 | Haugholt et al. | 356/338 |
| 2003/0169418 A1 * | 9/2003 | Fujii et al. | 356/237.2 |
| 2008/0018892 A1 | 1/2008 | Haugholt et al. | |

* cited by examiner

DEVICE AND METHOD FOR CONTACTLESS DETECTION OF CHARACTERISTICS OF CONTINUOUSLY DELIVERED TRANSLUCENT PRODUCTS

CROSS-REFERENCE TO RELATED APPLICATIONS

This application is a National Stage Application of PCT/EP2009/001359, filed Feb. 20, 2009, which designates the United States and claims the priority of German Patent Application 10 2008 013 525.9, filed Mar. 8, 2008.

BACKGROUND OF THE INVENTION

The invention concerns an apparatus for the contactless detection of characteristics of continuously conveyed, translucent products, comprising firstly a transmitting unit having a light source for generating high-intensity light radiation, a light-converting element for forming a planar light field from the light radiation and a focusing element for forming a line of light running transversely to the direction of conveying F of the products from the planar light field, and secondly a receiving unit having a detection device for picking up the light radiation transflected by the product, wherein a shading element is arranged between the transmitting unit and the receiving unit.

Furthermore the invention concerns a method for the contactless detection of characteristics of continuously conveyed, translucent products, comprising the steps of: continuously conveying the products through an inspection region of a receiving unit, exposing the products to light radiation by a transmitting unit, and picking up the light radiation transflected by the products by the receiving unit.

Such apparatuses and methods are used in different industrial fields in which products are tested for certain characteristics. Possible characteristics are different product-specific properties, but also anomalies or foreign bodies and the like. In the fish-processing industry e.g. the detection of parasites inside fish fillets is of particular importance. This means that each fish fillet is tested for parasites, which are usually very small objects compared with the fish fillet. In this case the fish fillets are conveyed continuously at a very high speed of e.g. 40 cm/s or more on a transport element through an inspection region of a detection means.

It is known that the products, hence the fish fillets in the case of this example, can be exposed to light radiation. The light radiation which is scattered and/or reflected inside the translucent product is detected via the detection device and evaluated. To put it another way, the light radiation penetrates the products, wherein the light radiation is scattered without direction or reflected directionally inside the product, e.g. on foreign bodies. In addition further processes such as e.g. absorption and fluorescence may alter the spectral characteristic of the light as well. This light radiation obtained as a result of transflection (transflectance/interactance) (scattered and/or directed) is hereinafter also referred to as transflected light. The transflected light is then detected by the detection device. Known apparatuses are constructed so that they have a transmitting unit with a light source, wherein the light source beams high-intensity light radiation to a light-converting element. Within the light-converting element, in which e.g. glass fibre bundles can be arranged, the light radiation is shaped and conducted from the light input opening to the light output opening. The light-converting element has a planar opening in the output region for the light radiation. For physical reasons the light radiation scatters on leaving the light-converting element. This scattered light then encounters the focusing element which is arranged beneath the light-converting element and which focuses the planar light field to a line of light which runs transversely to the direction of conveying F of the products. In the known apparatuses, the transmitting unit is arranged either in front of the receiving unit or behind the receiving unit in the direction of conveying F of the products.

The problem with the existing apparatuses lies in that the single transmitting unit and hence the single light source on the one hand has too low a light intensity to illuminate/transilluminate the products sufficiently at high speeds of conveying, and on the other hand illuminates only a limited region of the fish fillet. This leads in particular to parts of the fish fillet, namely either in the leading region or in the trailing region, not being illuminated, as a result of which a full inspection is impossible.

SUMMARY OF THE INVENTION

It is therefore an object of the present invention to provide an apparatus which reliably ensures the detection of characteristics of translucent products at a high speed of conveying the products. Furthermore it is an object of the invention to propose a corresponding method.

This object is achieved by an apparatus having the features mentioned hereinbefore wherein at least two transmitting units with corresponding structure are provided, such that at least two independent light sources for illuminating the product are provided, and wherein one transmitting unit is arranged in front of the receiving unit in the direction of conveying F of the products and the other transmitting unit is arranged behind the receiving unit in the direction of conveying F. Hence in a surprisingly simple and reliable manner, illumination of the whole product is ensured. In addition to increasing the light intensity by a plurality of light sources, the arrangement of light sources according to the invention also ensures that the product is sufficiently illuminated over the entire area. Both when the products enter the inspection region and when they leave the inspection region, exposure to light of the product to be inspected is ensured. Also the increased light intensity ensures improved transillumination of the product. In other words, the light penetrates the products deeply.

An appropriate development of the invention provides that the two transmitting units are shielded from the receiving unit by a shading element. This ensures that light radiation which is scattered by the lenses in the direction of the inspection region is reliably shielded, so that the possibility of impairing pick-up of the light reflected by or, to be more precise, from the product and/or by the transport element and/or by the apparatus itself is excluded.

Each transmitting unit may be assigned at least two shading elements, such that the transmitting units are shielded by a shading element on either side. This construction prevents scattered light from impairing the inspection region on the side facing away from the receiving unit.

In one embodiment the focusing element is a cylindrical lens. Hence linear light radiation may be generated in a simple manner, so that the products are exposed to light across their whole width transversely to the direction of conveying F when passing through the inspection region.

In another embodiment the lenses of the two transmitting units may be oriented parallel to each other. Hence optimum illumination of the inspection region may be achieved for the whole product. In other words, an illumination-free section of the continuously conveyed product may be prevented with the described embodiment.

In a further embodiment the distance between the two lines of light generated by the light sources or lenses may be approximately 40 mm. Thereby the above-mentioned advantage may be supported even further.

The object may also be achieved by a method having the steps mentioned hereinbefore by the fact that the products are exposed to high-intensity light radiation from separate light sources both on entering the inspection region of a detection device of the receiving unit and on leaving the inspection region of the detection device. The resulting advantages have already been described in connection with the apparatus, so that reference is made to the appropriate passages to avoid repetition.

BRIEF DESCRIPTION OF THE DRAWINGS

Further features and developments are apparent from the following description considered in conjunction with the attached drawings.

DETAILED DESCRIPTION

The apparatuses described serve to detect parasites in fish fillets. The apparatus is, however, equally suitable for the detection of characteristics of other translucent products.

Figure 1:
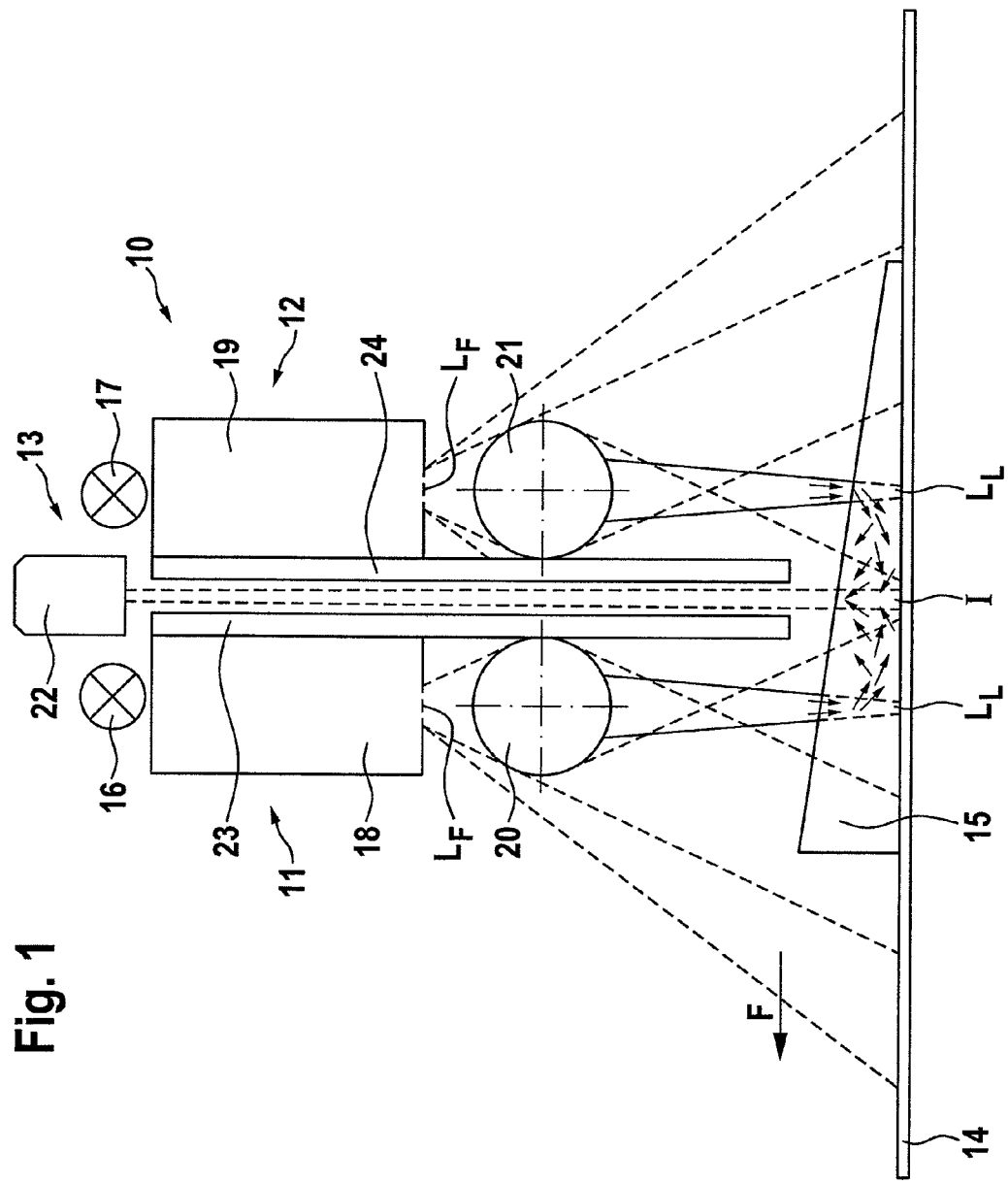
FIG. 1 is a schematic view of a first embodiment of the apparatus according to the invention in a front view.

The apparatus 10 shown in FIG. 1 comprises a first transmitting unit 11, a second transmitting unit 12 and a receiving unit 13. The apparatus 10 may be arranged above a transport element 14. Arrangement beneath the transport element 14 is also possible. On the transport element 14 the products 15 may be conveyed continuously and at high speed in the direction of conveying F, wherein the direction of conveying F may also be reversed.

Figure 3:
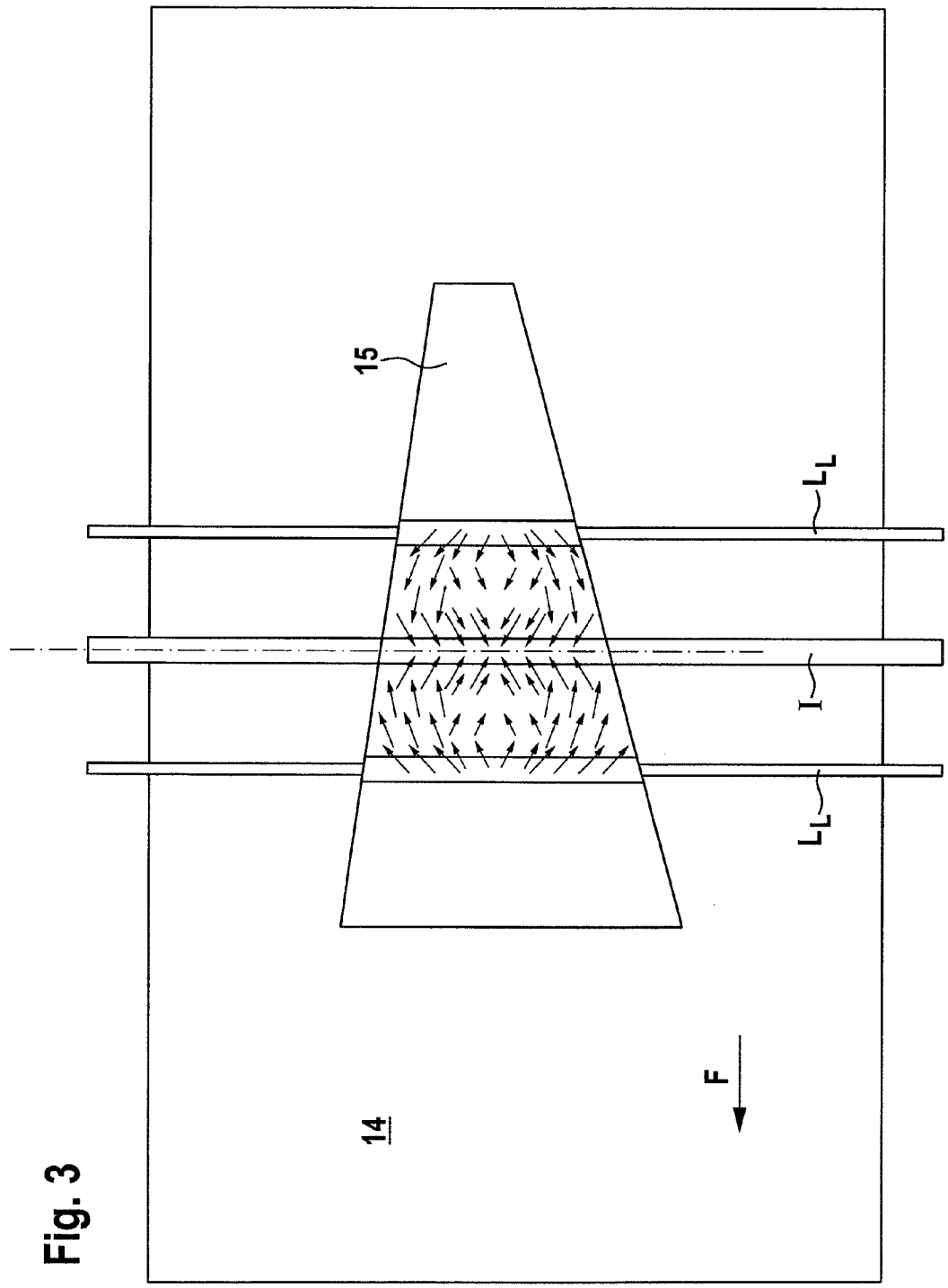
FIG. 3 is a top view of a product to be inspected with lines of light shown and inspection region shown.

Each transmitting unit 11, 12 has a light source 16 or 17 for generating high-intensity light radiation, a light-converting element 18 or 19 for forming a planar light field from the light radiation emanating from the light sources 16, 17, and a focusing element 20 or 21 for forming a line of light $L_L$ running transversely to the direction of conveying F of the products 14 from the planar light field. See FIG. 3. The receiving unit 13 has a detection device 22 which can be, for example, a camera or the like. Each light source 16, 17 can be arranged inside or outside the light-converting element 18, 19 and be composed for example of a plurality, preferably three, halogen lamps for example, with a power of 150 W each and a colour temperature of approximately 3200 K) with associated reflectors.

In the embodiment shown in FIG. 1, between the transmitting units 11, 12 and the receiving unit 13 is provided one shading element 23 or 24 each. The shading elements 23, 24 are light-impermeable and extend transversely to the direction of conveying F across the full width of the apparatus 10 and vertically to the plane of conveying from the detection device 22 to just above the products 15 to be inspected. The length of the shading elements 23, 24 can vary particularly in the vertical dimension.

The separate transmitting units 11, 12 may be arranged on both sides of the receiving unit 13. In the direction of conveying F of the products 15, one of the transmitting units 11, 12 may be arranged in front of the receiving unit 13 and the other transmitting unit 12, 11 may be arranged behind the receiving unit 13. Thus the receiving unit 13 may in each case be sandwiched between the transmitting units 11, 12, separated by the shading elements 23, 24. Further arrangements of the transmitting units 11, 12 in relation to the receiving unit 13, for example offset from the receiving unit 13, are possible too. As already mentioned, both transmitting units 11, 12 may be arranged above the transport element 14. But also possible is an arrangement of both transmitting units 11, 12 beneath the transport element 14, which is then light-permeable, or a variable arrangement with one transmitting unit 11 or 12 above and one transmitting unit 12 or 11 below the transport element 14.

The focusing elements 20, 21 may be constructed as a cylindrical lens. The design and dimensions of the lenses can vary. A lens having a diameter of approximately 25 mm and a length of approximately 200 mm may be provided. The lenses may be made of poly(meth)acrylates. Other suitable materials are also possible, however. The lenses may in each case be releasably attached to the light-converting element 18, 19, for example by clamps or the like. The lenses may run parallel to each other. In other words, the centre axes of both lenses are oriented transversely to the direction of conveying F of the products 15. The distance between the lenses can vary dependent on different factors (e.g. product size). The distance may be selected such that the lines of light $L_L$ generated by the light sources 16, 17 or the light-converting elements 18, 19 and the focusing elements 20, 21 have a distance of approximately 40 mm between them.

The detection device 22 may comprise a camera. Optionally, a sensor unit can be provided as well. Naturally all other known elements for receiving signals and in particular for detecting and picking up transflected light can be used as well. The detection device 22 can also be a spectrometer with spatial resolution. A spectrometer with 128 spectral bands within a range from 400 to 1000 nm and a spatial resolution of approximately 0.5 mm² (0.5 mm transversely to the direction of conveying F and 1 mm in the direction of conveying F) may be provided. The speed of reading may be 400 Hz. The spectrometer may be arranged at a given distance from the transport element 14. The distance can vary, but is preferably approximately 1000 mm. The detection device 22 can be assigned an evaluating unit (not shown). Part of the evaluating unit can also be a computer unit and/or a control unit by which a reaction can be given to the results evaluated, for example to separate out unwanted or defective products or the like.

In the embodiments described, the light-converting element 18, 19 may be a cuboid box with the dimensions of width×height×length of 25×100×200 mm. Of course, the dimensions are variable almost as desired. The box may be made of a light-impermeable material such as e.g. aluminium painted black, and has in the interior a plurality of, for example three glass fibre bundles. The box has a light input opening. In the region of this light input opening may be arranged the light source 16, 17. Furthermore, the box has a light output opening which may be formed on the side facing towards the lenses. The light output opening may be rectangular, so that the light conducted by the glass fibre bundles from the light input opening to the light output opening emerges from the box in a planar light field $L_F$ (or light band). The size and shape of the light output opening can of course vary. In addition to the described embodiment, other designs and constructions of the light-converting element 18, 19 are possible as well.

Figure 2:
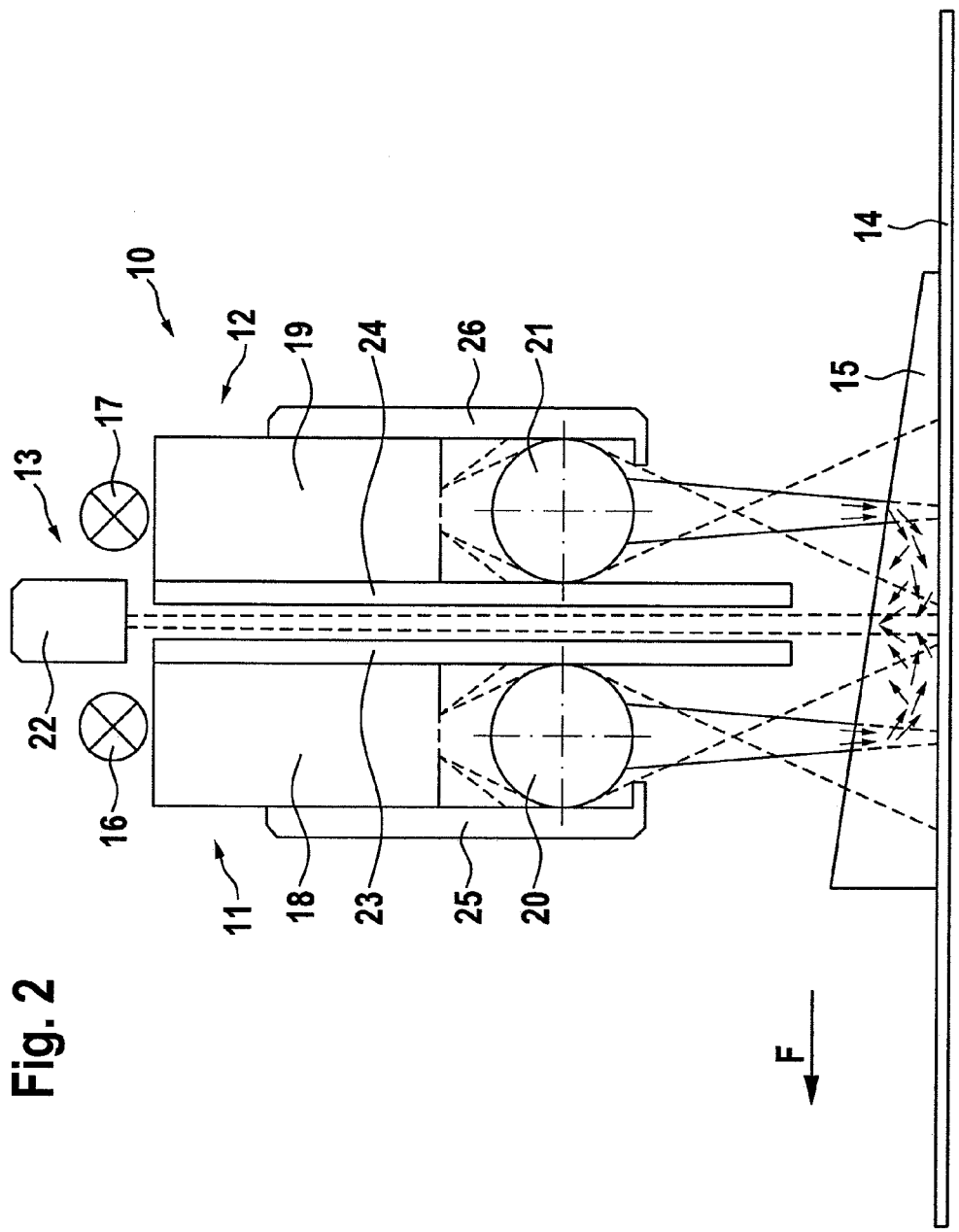
FIG. 2 is a schematic view of a further embodiment of the apparatus according to the invention in a front view.

In further embodiments e.g. additional shading elements 25 or 26 may be provided. In the embodiment according to FIG. 2, each transmitting unit 11, 12 may be assigned at least two shading elements 23 and 25 or 24 and 26. The shading elements 23, 24 serve to shield the lenses on the side facing towards the inspection region. The shading elements 25, 26 serve to shield the lenses on the opposite side. All of the shading elements 23 to 26 may be made of aluminium painted black. But other designs are possible as well. In the event that only the shading elements 23, 24 facing towards the inspection region I are provided, these extend to just above the products to be conveyed. The shading elements 25, 26 facing away from the inspection region I have, in addition to the vertically extending sections, a horizontally extending section which partly shields the lenses on the lower side. In general the shading elements 23 to 26 serve to reduce the light scattered by the lenses.

The principle of the method is described below with the aid of the figures. The products 15, that is, for example the fish fillets, are conveyed at high speed in the direction of conveying F on the transport element 14. When the products 15 enter the inspection region I, the leading section of the product 15 is already exposed to light from transmitting unit 12, so that the receiving unit 13 can pick up transflected light, that is, light which is reflected within the product, scattered and/or directed. The continuously conveyed product 15 is then conveyed on through the inspection region I to the output region. When the trailing section of the product 15 is still in the inspection region I, the trailing region is exposed to light from transmitting unit 11. In between, both transmitting units 11, 12 illuminate the product 15 in parallel.

The arrangement of the apparatus 10 accordingly ensures that the products to be inspected are fully illuminated on the one hand, and on the other hand this illumination also takes place with the necessary intensity. The products 15 can also be conveyed in the reverse direction of conveying.

The invention claimed is:

1. An apparatus for contactless detection of characteristics of continuously conveyed, translucent products, comprising:
   first and second transmitting units each having
      an independent light source to generate high-intensity light radiation to illuminate the product,
      a light-converting element to form a planar light field from the light radiation, and
      a focusing element to form a line of light from the planar light field, wherein the line of light extends transversely to a direction of conveying of the products and parallel to the line of light generated by the other transmitting unit, wherein the line of light and a center axis of the focussing element define a first plane perpendicular to the direction of conveying;
   a receiving unit having a detection device to pick up the light radiation transflected by the product in an inspection region, wherein the line of light formed by each transmitting unit runs parallel to the inspection region, and wherein the detection device and the inspection region define a second plane parallel to the first plane; and
   shading elements arranged respectively between the transmitting units and the receiving unit, wherein the first and second transmitting units are shielded from the receiving unit by the respective shading elements,
   wherein the first transmitting unit is arranged in front of the receiving unit in the direction of conveying of the products and the second transmitting unit is arranged behind the receiving unit in the direction of conveying.

2. The apparatus according to claim 1, wherein the receiving unit is sandwiched between the shading elements which are directed vertically to a plane of conveying of the products.

3. The apparatus according to claim 1, wherein at least two shading elements are assigned to each transmitting unit such that the transmitting units are shielded by a shading element on either side.

4. The apparatus according to claim 1, wherein the focusing element comprises a cylindrical lens.

5. The apparatus according to claim 4, wherein the lens comprises poly(meth)acrylates.

6. The apparatus according to claim 4, wherein the lens has a diameter of 25 mm and a length of 200 mm.

7. The apparatus according to claim 4, wherein the lens is attached to the light-converting element.

8. The apparatus according to claim 4, wherein the lenses of the two transmitting units are oriented parallel to each other.

9. The apparatus according to claim 4, wherein the lenses have centre axes that are oriented transversely to the direction of conveying of the products.

10. The apparatus according to claim 1, wherein a distance between the two lines of light generated by the light sources or lenses is approximately 40 mm.

11. The apparatus according to claim 1, wherein the detection device comprises a camera.

12. The apparatus according to claim 1, further comprising an evaluation unit assigned to the detection device.

13. The apparatus according to claim 1, wherein the light-converting element is constructed to form a rectangular light field.

14. The apparatus according to claim 1, further including a transport element for conveying the products, and wherein both transmitting units are arranged above the transport element.

15. A method for contactless detection of characteristics of continuously conveyed, translucent products, comprising the steps of:
   continuously conveying the products through the inspection region of the detection device of the receiving unit of the apparatus of claim 1;
   exposing the products to high-intensity light radiation from the independent light sources of the first and second transmitting units both on entering the inspection region and on leaving the inspection region of the detection device; and
   picking up the light radiation transflected by the products by the receiving unit.

16. The method according to claim 15, wherein the exposing includes widening the high-intensity light radiation emanating from each of the light sources into the planar light fields by the light-converting elements and then focussing the planar light by the focusing elements into the lines of light running transversely to the direction of conveying of the products.

17. The method according to claim 15, including shielding the first and second transmitting units on at least two sides.

18. The method according to claim 15, including processing the transflected light radiation picked up by the receiving unit in an evaluating unit.

19. The apparatus according to claim 1, wherein the center axes of the focussing elements are oriented transversely to the direction of conveying, and wherein a distance between the center axes of the focusing elements is equal to a distance between the lines of light generated by the first and second transmitting units.

* * * * *

UNITED STATES PATENT AND TRADEMARK OFFICE
CERTIFICATE OF CORRECTION

| | |
|---|---|
| PATENT NO. | : 8,339,596 B2 |
| APPLICATION NO. | : 12/919825 |
| DATED | : December 25, 2012 |
| INVENTOR(S) | : Sivertsen et al. |

It is certified that error appears in the above-identified patent and that said Letters Patent is hereby corrected as shown below:

Specification:

At column 3, line 54, change "for" to -- (for --.

Claims:

At column 6, claim 16, line 51, after "light" insert -- fields --.

Signed and Sealed this
Thirteenth Day of August, 2013

Teresa Stanek Rea
*Acting Director of the United States Patent and Trademark Office*